(12) United States Patent
Ulrich et al.

(10) Patent No.: US 11,911,595 B2
(45) Date of Patent: Feb. 27, 2024

(54) SYSTEMS AND METHODS FOR AUTOMATED INSULIN DELIVERY RESPONSE TO MEAL ANNOUNCEMENTS

(71) Applicant: Tandem Diabetes Care, Inc., San Diego, CA (US)

(72) Inventors: Thomas R. Ulrich, Oceanside, CA (US); Virginia S. Lu, San Diego, CA (US)

(73) Assignee: TANDEM DIABETES CARE, INC., San Diego, CA (US)

( * ) Notice: Subject to any disclaimer, the term of this patent is extended or adjusted under 35 U.S.C. 154(b) by 165 days.

(21) Appl. No.: 17/323,529

(22) Filed: May 18, 2021

(65) Prior Publication Data

US 2021/0353857 A1    Nov. 18, 2021

Related U.S. Application Data

(60) Provisional application No. 63/026,303, filed on May 18, 2020.

(51) Int. Cl.
*A61M 5/172*    (2006.01)
*A61M 5/142*    (2006.01)

(52) U.S. Cl.
CPC .......... *A61M 5/1723* (2013.01); *A61M 5/142* (2013.01); *A61M 2005/14208* (2013.01); *A61M 2205/3553* (2013.01); *A61M 2205/502* (2013.01); *A61M 2230/201* (2013.01)

(58) Field of Classification Search
CPC ................ A61M 5/1723; A61M 5/142; A61M 2005/14208; A61M 2205/3553; A61M 2205/502; A61M 2230/201; A61M 5/14; A61M 5/172; A61M 5/168
See application file for complete search history.

(56) References Cited

U.S. PATENT DOCUMENTS

| | | |
|---|---|---|
| 4,919,596 A | 4/1990 | Slate et al. |
| 5,256,157 A | 10/1993 | Samiotes et al. |
| 5,368,555 A | 11/1994 | Sussman et al. |
| 5,391,250 A | 2/1995 | Cheney, II et al. |
| 5,460,605 A | 10/1995 | Tuttle et al. |
| 5,569,186 A | 10/1996 | Lord et al. |
| 5,810,771 A | 9/1998 | Blomquist |
| 5,935,099 A | 8/1999 | Peterson et al. |
| 5,976,780 A | 11/1999 | Shah |
| 6,280,408 B1 | 8/2001 | Sipin |
| 6,381,493 B1 | 4/2002 | Stadler et al. |
| 6,387,069 B1 | 5/2002 | Utterberg |
| 6,589,229 B1 | 7/2003 | Connelly |

(Continued)

FOREIGN PATENT DOCUMENTS

EP    1720601 A1    9/2005

*Primary Examiner* — Jason E Flick
(74) *Attorney, Agent, or Firm* — MERCHANT & GOULD P.C.

(57) ABSTRACT

Disclosed herein are apparatuses and methods that account for meal announcements in closed loop insulin delivery systems. Rather than simply increasing an insulin delivery rate in response to the meal announcement, the closed loop algorithm can be modified to increase the insulin on board tolerance during eating periods. This approach utilizes the stability of the cascaded loop in the closed loop algorithm to prevent the oscillations in glucose levels that can occur by simply increasing the basal rate.

20 Claims, 7 Drawing Sheets

(56) References Cited

U.S. PATENT DOCUMENTS

| | | |
|---|---|---|
| 7,060,059 B2 | 6/2006 | Keith et al. |
| 7,073,485 B2 | 7/2006 | Truscott et al. |
| 7,416,541 B2 | 8/2008 | Yuzhakov et al. |
| 7,429,255 B2 | 9/2008 | Thompson |
| 7,503,903 B2 | 3/2009 | Carlisle et al. |
| 7,654,976 B2 | 2/2010 | Peterson et al. |
| 7,660,615 B2 | 2/2010 | VanAntwerp et al. |
| 7,806,886 B2 | 10/2010 | Kanderian, Jr. et al. |
| 7,904,162 B2 | 3/2011 | Whitehurst et al. |
| 7,944,366 B2 | 5/2011 | Krulevitch et al. |
| 8,002,700 B2 | 8/2011 | Ferek-Petric et al. |
| 8,147,448 B2 | 4/2012 | Sundar et al. |
| 8,273,052 B2 | 9/2012 | Damiano et al. |
| 8,313,308 B2 | 11/2012 | Lawless et al. |
| 8,409,133 B2 | 4/2013 | Pesach et al. |
| 8,454,576 B2 | 6/2013 | Mastrototaro et al. |
| 8,467,980 B2 | 6/2013 | Campbell et al. |
| 8,475,409 B2 | 7/2013 | Tsoukalis |
| 8,579,879 B2 | 11/2013 | Palerm et al. |
| 8,585,593 B2 | 11/2013 | Kovatchev et al. |
| 8,679,016 B2 | 3/2014 | Mastrototaro et al. |
| 9,089,305 B2 | 7/2015 | Hovorka |
| 9,320,471 B2 | 4/2016 | Hayes et al. |
| 9,440,025 B2 | 9/2016 | Kanderian, Jr. et al. |
| 9,483,615 B2 | 11/2016 | Roberts |
| 9,486,171 B2 | 11/2016 | Saint |
| 9,757,510 B2 | 9/2017 | Finan |
| 10,016,561 B2 | 7/2018 | Saint et al. |
| 10,420,489 B2 | 9/2019 | Kovatchev et al. |
| 10,493,202 B2 | 12/2019 | Hayter |
| 10,549,036 B2 | 2/2020 | Starkweather et al. |
| 10,712,170 B2 | 7/2020 | Cantwell et al. |
| 10,850,033 B2 | 12/2020 | Kovelman |
| 10,856,786 B2 | 12/2020 | Steil et al. |
| 10,872,102 B2 | 12/2020 | Wei et al. |
| 10,918,789 B2 | 2/2021 | Bryant, Jr. et al. |
| 11,083,843 B2 | 8/2021 | Hayter et al. |
| 11,097,051 B2 | 8/2021 | Wu et al. |
| 11,246,986 B2 | 2/2022 | Wilinska et al. |
| 11,376,362 B2 | 7/2022 | Mazlish |
| 11,395,877 B2 | 7/2022 | Kamen et al. |
| 11,471,598 B2 | 10/2022 | Estes |
| 11,707,567 B2 | 7/2023 | Kamen et al. |
| 11,751,779 B2 | 9/2023 | Kovatchev et al. |
| 2003/0208113 A1 | 11/2003 | Mault et al. |
| 2007/0061735 A1 | 3/2007 | Hoffberg et al. |
| 2008/0228056 A1 | 9/2008 | Blomquist et al. |
| 2008/0269723 A1 | 10/2008 | Mastrototaro et al. |
| 2010/0145262 A1 | 6/2010 | Bengtsson et al. |
| 2010/0174228 A1 | 7/2010 | Buckingham et al. |
| 2010/0298765 A1* | 11/2010 | Budiman ............ A61B 5/1495 604/66 |
| 2011/0071464 A1 | 3/2011 | Palerm |
| 2013/0046281 A1 | 2/2013 | Javitt |
| 2016/0030669 A1 | 2/2016 | Harris et al. |
| 2017/0189614 A1* | 7/2017 | Mazlish ............ A61M 5/1723 |
| 2019/0388015 A1 | 12/2019 | Blomquist |
| 2020/0101226 A1 | 4/2020 | Rosinko et al. |
| 2020/0171249 A1 | 6/2020 | Rosinko |
| 2020/0179603 A1 | 6/2020 | Rosinko |
| 2020/0254174 A1 | 8/2020 | Kruse et al. |
| 2020/0368430 A1 | 11/2020 | Ulrich et al. |
| 2021/0001038 A1 | 1/2021 | Rosinko |
| 2021/0001044 A1 | 1/2021 | Michaud et al. |
| 2021/0012875 A1 | 1/2021 | Blomquist et al. |
| 2021/0012876 A1 | 1/2021 | Blomquist |
| 2021/0113766 A1 | 4/2021 | Kearns et al. |
| 2021/0137427 A1* | 5/2021 | Cardinali ............ A61M 5/1723 |
| 2021/0154405 A1 | 5/2021 | Kearns et al. |
| 2021/0193288 A1 | 6/2021 | Blomquist |
| 2021/0259590 A1* | 8/2021 | Metzmaker ............ G16H 40/67 |
| 2021/0402091 A1 | 12/2021 | Harris |
| 2022/0134001 A1 | 5/2022 | Ulrich et al. |
| 2023/0034283 A1 | 2/2023 | Michaud et al. |

\* cited by examiner

SYSTEMS AND METHODS FOR AUTOMATED INSULIN DELIVERY RESPONSE TO MEAL ANNOUNCEMENTS

RELATED APPLICATION

The present application claims the benefit of U.S. Provisional Application No. 63/026,303 filed May 18, 2020, which is hereby incorporated herein in its entirety by reference.

FIELD OF THE INVENTION

The present invention relates generally to ambulatory infusion pumps and, more particularly, to operation of ambulatory infusion pumps in a closed-loop or semi-closed-loop fashion.

BACKGROUND OF THE INVENTION

There are a wide variety of medical treatments that include the administration of a therapeutic fluid in precise, known amounts at predetermined intervals. Devices and methods exist that are directed to the delivery of such fluids, which may be liquids or gases, are known in the art.

One category of such fluid delivery devices includes insulin injecting pumps developed for administering insulin to patients afflicted with type I, or in some cases, type II diabetes. Some insulin injecting pumps are configured as portable or ambulatory infusion devices can provide continuous subcutaneous insulin injection and/or infusion therapy as an alternative to multiple daily injections of insulin via a syringe or an insulin pen. Such pumps are worn by the user and may use replaceable cartridges. In some embodiments, these pumps may also deliver medicaments other than, or in addition to, insulin, such as glucagon, pramlintide, and the like. Examples of such pumps and various features associated therewith include those disclosed in U.S. Patent Publication Nos. 2013/0324928 and 2013/0053816 and U.S. Pat. Nos. 8,287,495; 8,573,027; 8,986,253; and 9,381,297, each of which is incorporated herein by reference in its entirety.

Ambulatory infusion pumps for delivering insulin or other medicaments can be used in conjunction with blood glucose monitoring systems, such as blood glucose meters (BGMs) and continuous glucose monitoring devices (CGMs). A CGM provides a substantially continuous estimated blood glucose level through a transcutaneous sensor that estimates blood analyte levels, such as blood glucose levels, via the patient's interstitial fluid CGM systems typically consist of a transcutaneously-placed sensor, a transmitter and a monitor.

Ambulatory infusion pumps typically allow the patient or caregiver to adjust the amount of insulin or other medicament delivered, by a basal rate or a bolus, based on blood glucose data obtained by a BGM or a CGM, and in some cases include the capability to automatically adjust such medicament delivery. Some ambulatory infusion pumps may include the capability to interface with a BGM or CGM such as, e.g., by receiving measured or estimated blood glucose levels and automatically adjusting or prompting the user to adjust the level of medicament being administered or planned for administration or, in cases of abnormally low blood glucose readings, reducing or automatically temporarily ceasing or prompting the user temporarily to cease or reduce insulin administration. These portable pumps may incorporate a BGM or CGM within the hardware of the pump or may communicate with a dedicated BGM or CGM via wired or wireless data communication protocols, directly and/or via a device such as a smartphone. One example of integration of infusion pumps with CGM devices is described in U.S. Patent Publication No. 2014/0276419, which is hereby incorporated by reference herein.

As noted above, insulin or other medicament dosing by basal rate and/or bolus techniques could automatically be provided by a pump based on readings received into the pump from a CGM device that is, e.g., external to the portable insulin pump or integrated with the pump as a pump-CGM system in a closed-loop or semi-closed-loop fashion. With respect to insulin delivery, some systems including this feature can be referred to as artificial pancreas systems because the systems serve to mimic biological functions of the pancreas for patients with diabetes. Such systems are also referred to as automated insulin delivery (AID) systems.

In some AID systems, a user can manually inform the algorithm that the user will be eating in what is often referred to as a "meal announcement." In response to a meal announcement, the algorithm will typically increase the basal rate being delivered to the user in anticipation of increased blood glucose levels due to the consumption of carbohydrates in the meal. However, increasing the basal rate in response to a meal announcement can subject the user to undesirable oscillations in glucose levels because the timing and amount of carbohydrates that will be consumed may be unknown.

SUMMARY

Disclosed herein are apparatuses and methods that account for meal announcements in closed loop insulin delivery systems. Rather than simply increasing an insulin delivery rate in response to the meal announcement, the closed loop algorithm can be modified to increase the insulin on board tolerance during eating periods. This approach utilizes the stability of the cascaded loop in the closed loop algorithm to prevent the oscillations in glucose levels that can occur by simply increasing the basal rate.

In an embodiment, a closed loop algorithm can be modified to include a pre-meal scale used in calculating a set point for insulin on board (IOB) used in a cascaded loop for calculating insulin doses for the patient based on CGM values. If the user enters a meal announcement indicating to the system that the user will be eating soon, the pre-meal scale can be activated to increase the IOB set point by a predetermined amount for calculating insulin doses for a predetermined time after the meal announcement. If the user has not made a meal announcement, the pre3-meal scale is not activated and does not affect the delivery calculation.

In an embodiment, a system for closed loop diabetes therapy includes a pump mechanism configured to facilitate delivery of insulin to a user, a communications device adapted to receive glucose levels from a continuous glucose monitor and a processor functionally linked to the pump mechanism and the communications device. The processor can be configured to calculate and deliver insulin doses to the user based on a closed loop insulin delivery algorithm that includes an outer glucose loop that compares glucose levels from the continuous glucose monitor to a glucose target to determine an insulin on board target for the user and an inner insulin on board loop that compares an estimated insulin on board for the user to the insulin on board target to determine an insulin on board error used to calculate insulin doses configured to maintain the insulin on board of the user at the insulin on board target and the glucose levels of the user at the glucose level target. If the processor receives an indication that the user will be eating a meal, a pre-meal scale for the closed loop insulin delivery algorithm can be activated that modifies the inner insulin on board loop of the closed loop delivery algorithm that calculates insulin doses to maintain the insulin on board of the user at the insulin on board target. Insulin doses can be calculated and delivered to the user based on glucose levels from the continuous glucose monitor using the pre-meal scale of the closed loop insulin delivery algorithm following the indication that the user will be eating the meal.

In an embodiment, a method of closed loop diabetes therapy includes receiving glucose levels of a user from a continuous glucose monitor and calculating insulin doses to the user based on a closed loop insulin delivery algorithm. The closed loop insulin delivery algorithm can include an outer glucose loop that compares glucose levels from the continuous glucose monitor to a glucose target to determine an insulin on board target for the user and an inner insulin on board loop that compares an estimated insulin on board for the user to the insulin on board target to determine an insulin on board error used to calculate insulin doses configured to maintain the insulin on board of the user at the insulin on board target and the glucose levels of the user at the glucose level target. The calculated insulin doses can be delivered to the user with a pump mechanism. Upon receiving an indication that the user will be eating a meal a pre-meal scale for the closed loop insulin delivery algorithm can be activated that modifies the inner insulin on board loop of the closed loop delivery algorithm that calculates insulin doses to maintain the insulin on board of the user at the insulin on board target. Insulin doses can be calculated and delivered to the user based on glucose levels from the continuous glucose monitor using the pre-meal scale of the closed loop insulin delivery algorithm following the indication that the user will be eating the meal.

The above summary is not intended to describe each illustrated embodiment or every implementation of the subject matter hereof. The figures and the detailed description that follow more particularly exemplify various embodiments.

BRIEF DESCRIPTION OF THE DRAWINGS

The invention may be more completely understood in consideration of the following detailed description of various embodiments of the invention in connection with the accompanying drawings, in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

Figure 1:
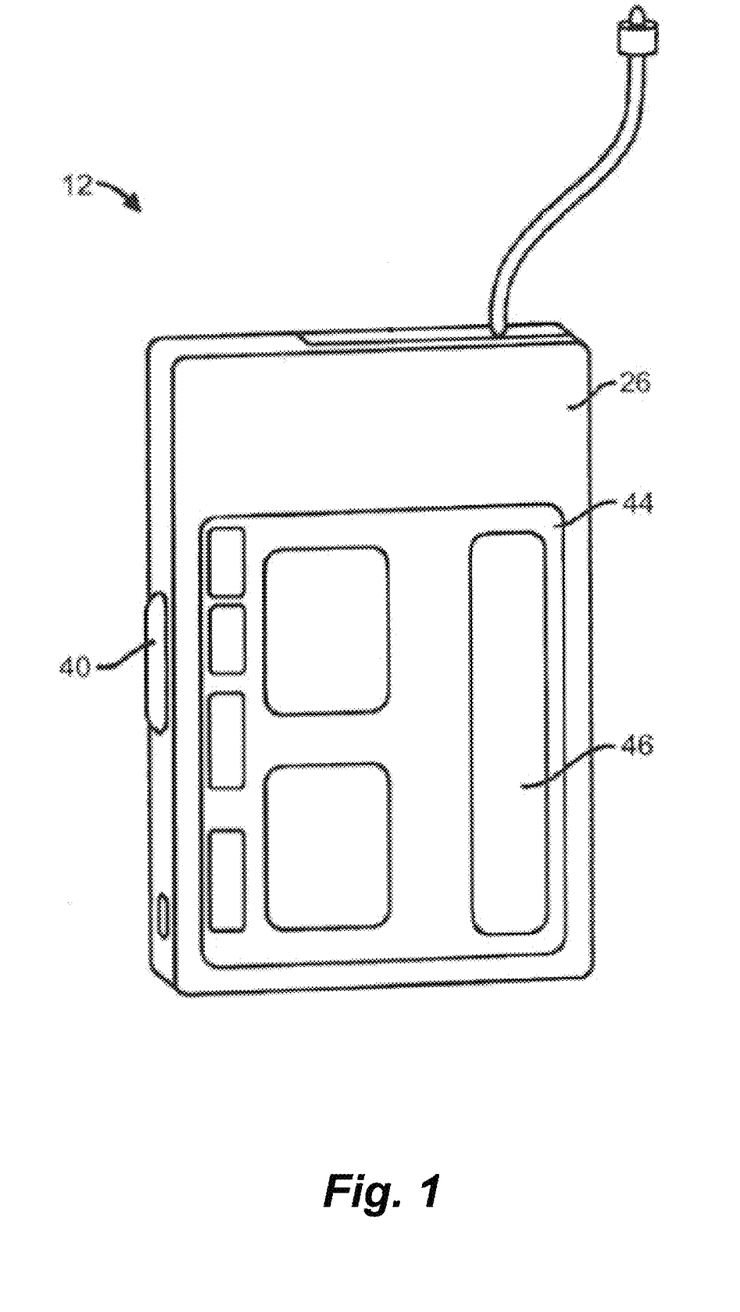
FIG. 1 is a medical device that can be used with embodiments of the disclosure.

FIG. 1 depicts an embodiment of a medical device according to the disclosure. In this embodiment, the medical device is configured as a pump 12. Pump 12 may be an infusion pump that includes a pumping or delivery mechanism and reservoir for delivering medicament to a patient and an output/display 44. The output/display 44 may include an interactive and/or touch sensitive screen 46 having an input device such as, for example, a touch screen comprising a capacitive screen or a resistive screen. The pump 12 may additionally or instead include one or more of a keyboard, a microphone or other input devices known in the art for data entry, some or all of which may be separate from the display. The pump 12 may also include a capability to operatively couple to one or more other display devices such as a remote display, a remote control device, a laptop computer, personal computer, tablet computer, a mobile communication device such as a smartphone, a wearable electronic watch or electronic health or fitness monitor, or personal digital assistant (PDA), a CGM display etc.

In one embodiment, the medical device can be an ambulatory insulin pump configured to deliver insulin to a patient. Further details regarding such pump devices can be found in U.S. Pat. No. 8,287,495, which is incorporated herein by reference in its entirety. In other embodiments, the medical device can be an infusion pump configured to deliver one or more additional or other medicaments to a patient.

Figure 2:
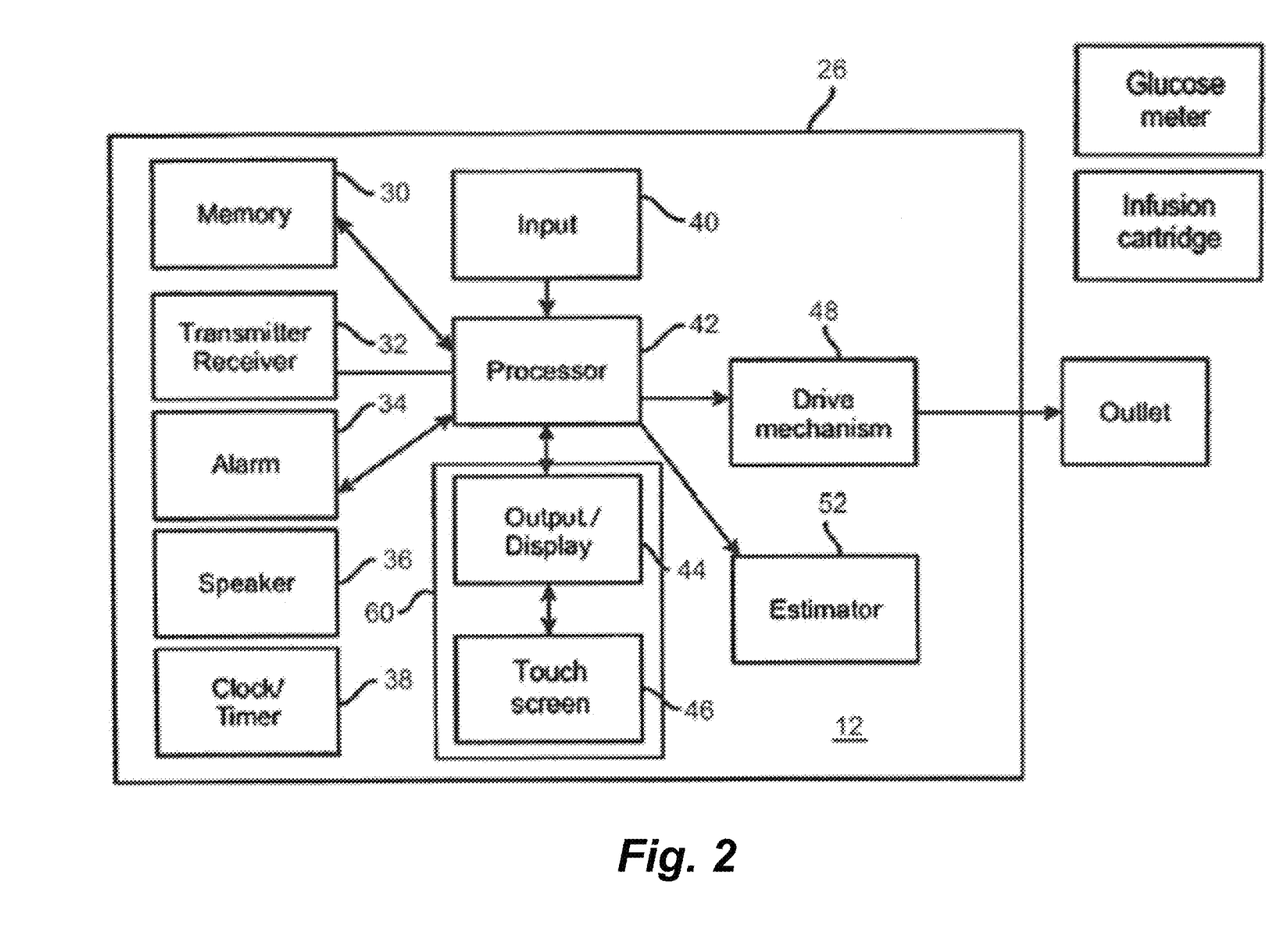
FIG. 2 is a block diagram representing a medical device that can be used with embodiments of the disclosure.

FIG. 2 illustrates a block diagram of some of the features that can be used with embodiments, including features that may be incorporated within the housing 26 of a medical device such as a pump 12. The pump 12 can include a processor 42 that controls the overall functions of the device. The infusion pump 12 may also include, e.g., a memory device 30, a transmitter/receiver 32, an alarm 34, a speaker 36, a clock/timer 38, an input device 40, a user interface suitable for accepting input and commands from a user such as a caregiver or patient, a drive mechanism 48, an estimator device 52 and a microphone (not pictured). One embodiment of a user interface is a graphical user interface (GUI) 60 having a touch sensitive screen 46 with input capability. In some embodiments, the processor 42 may communicate with one or more other processors within the pump 12 and/or one or more processors of other devices, for example, a continuous glucose monitor (CGM), display device, smartphone, etc. through the transmitter/receiver. The processor 42 may also include programming that may allow the processor to receive signals and/or other data from an input device, such as a sensor that may sense pressure, temperature or other parameters.

Figures 3A, 3B:
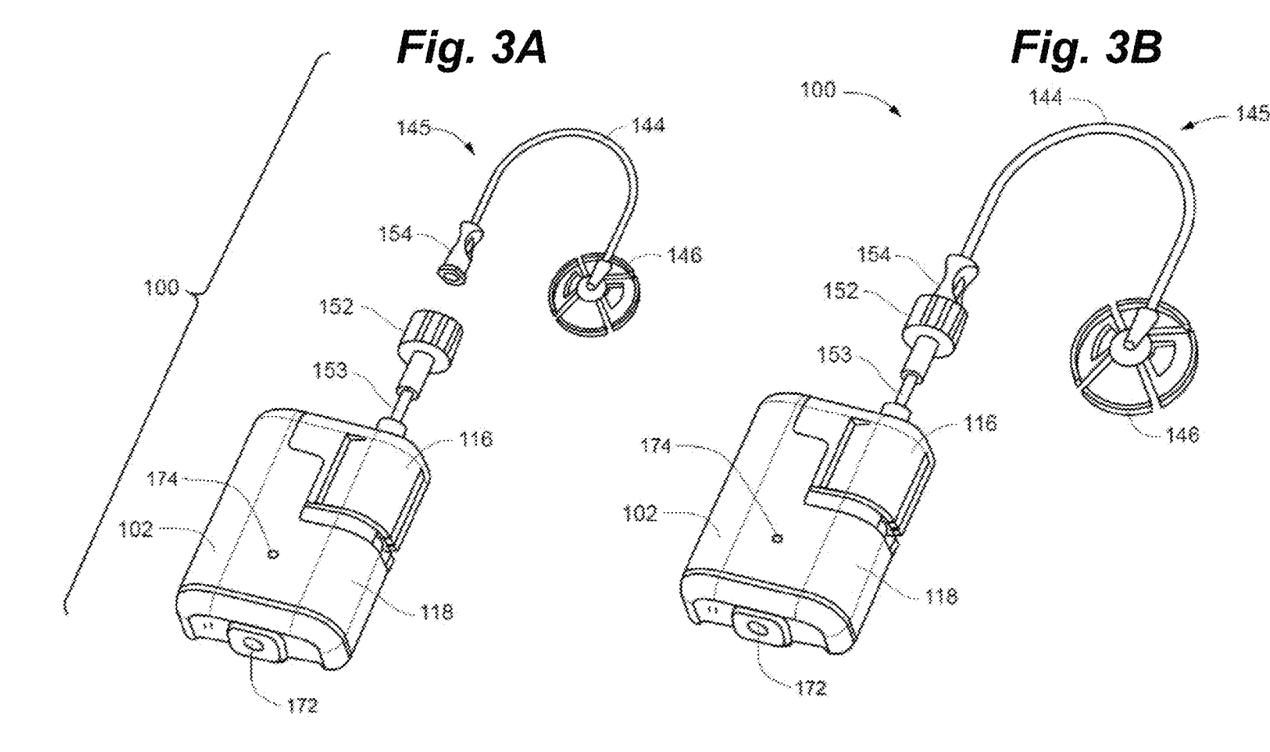
FIGS. 3A-3B depict an embodiment of a pump system according to the disclosure.

FIGS. 3A-3B depict another pump system including a pump 102 that can be used with embodiments. Drive unit 118 of pump 102 includes a drive mechanism 122 that mates with a recess in disposable cartridge 116 of pump 102 to attach the cartridge 116 to the drive unit 118. Pump system 100 can further include an infusion set 145 having a connector 154 that connects to a connector 152 attached to pump 102 with tubing 153. Tubing 144 extends to a site connector 146 that can attach or be pre-connected to a cannula and/or infusion needle that punctures the patient's skin at the infusion site to deliver medicament from the pump 102 to the patient via infusion set 145. In some embodiments, pump can include a user input button 172 and an indicator light 174 to provide feedback to the user.

In one embodiment, pump 102 includes a processor that controls operations of the pump and, in some embodiments, may receive commands from a separate device for control of operations of the pump. Such a separate device can include, for example, a dedicated remote control or a smartphone or other consumer electronic device executing an application configured to enable the device to transmit operating commands to the processor of pump 102. In some embodiments, processor can also transmit information to one or more separate devices, such as information pertaining to device parameters, alarms, reminders, pump status, etc. In one embodiment pump 102 does not include a display but may include one or more indicator lights 174 and/or one or more input buttons 172. Pump 102 can also incorporate any or all of the features described with respect to pump 12 in FIG. 2. Further details regarding such pumps can be found in U.S. Pat. No. 10,279,106 and U.S. Patent Publication Nos. 2016/0339172 and 2017/0049957, each of which is hereby incorporated herein by reference in its entirety.

Figure 4:
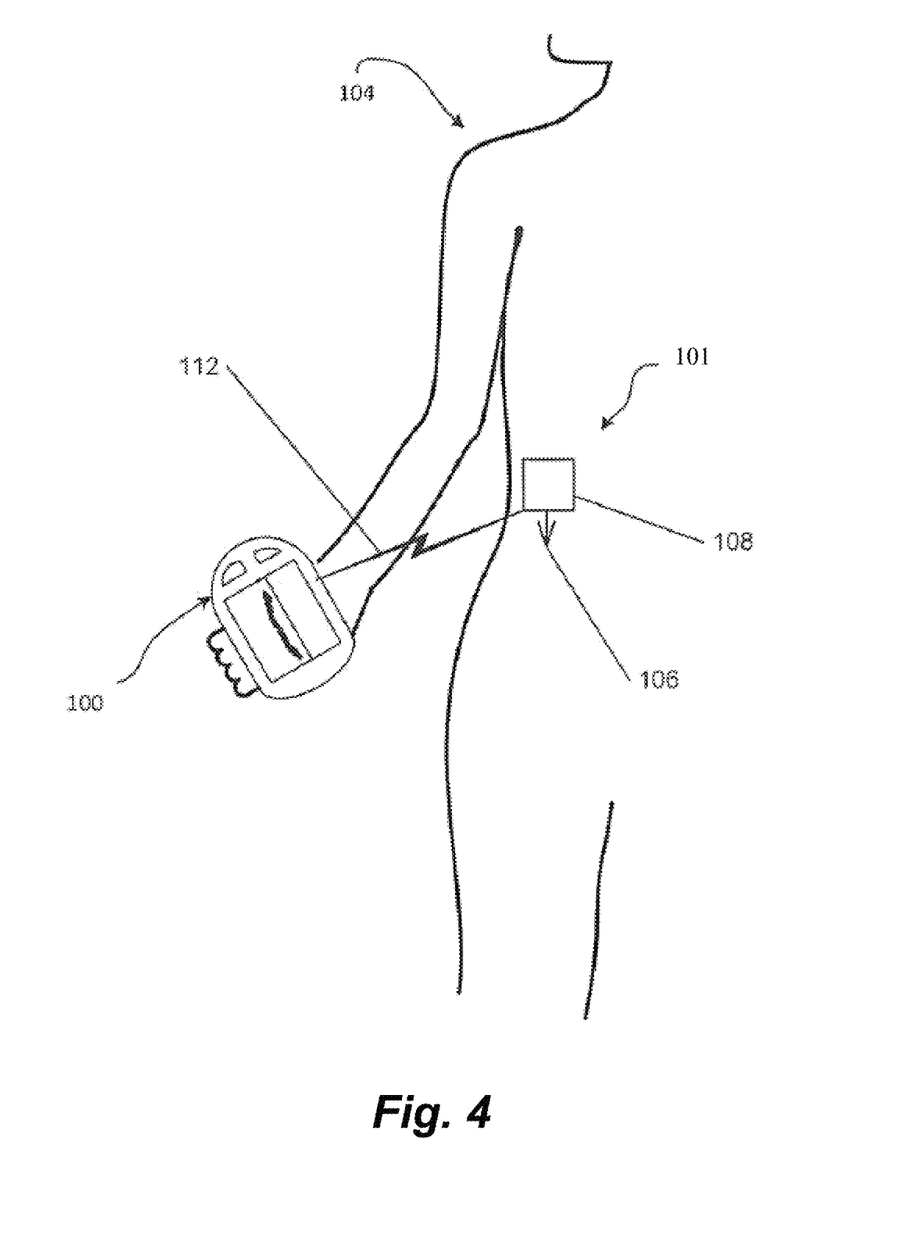
FIG. 4 is a schematic representation of a system according to the disclosure.

Pump 12 or 102 can interface directly or indirectly (via, e.g., a smartphone or other device) with a glucose meter, such as a blood glucose meter (BGM) or a continuous glucose monitor (CGM). Referring to FIG. 4, an exemplary CGM system 100 according to an embodiment of the present invention is shown (other CGM systems can be used). The illustrated CGM system includes a sensor 101 affixed to a patient 104 that can be associated with the insulin infusion device in a CGM-pump system. The sensor 101 includes a sensor probe 106 configured to be inserted to a point below the dermal layer (skin) of the patient 104. The sensor probe 106 is therefore exposed to the patient's interstitial fluid or plasma beneath the skin and reacts with that interstitial fluid to produce a signal that can be associated with the patient's blood glucose (BG) level. The sensor 101 includes a sensor body 108 that transmits data associated with the interstitial fluid to which the sensor probe 106 is exposed. The data may be transmitted from the sensor 101 to the glucose monitoring system receiver 100 via a wireless transmitter, such as a near field communication (NFC) radio frequency (RF) transmitter or a transmitter operating according to a "Wi-Fi" or Bluetooth® protocol, Bluetooth® low energy protocol or the like, or the data may be transmitted via a wire connector from the sensor 101 to the monitoring system 100. Transmission of sensor data to the glucose monitoring system receiver by wireless or wired connection is represented in FIG. 4 by the arrow line 112. Further detail regarding such systems and definitions of related terms can be found in, e.g., U.S. Pat. Nos. 8,311,749, 7,711,402 and 7,497,827, each of which is hereby incorporated by reference in its entirety.

In an embodiment of a pump-CGM system having a pump 12, 102 that communicates with a CGM and that integrates CGM data and pump data as described herein, the CGM can automatically transmit the glucose data to the pump. The pump can then automatically determine therapy parameters and deliver medicament based on the data. Such an automatic pump-CGM system for insulin delivery can be referred to as an automated insulin delivery (AID) or an artificial pancreas system that provides closed-loop therapy to the patient to approximate or even mimic the natural functions of a healthy pancreas. In such a system, insulin doses are calculated based on the CGM readings (that may or may not be automatically transmitted to the pump) and are automatically delivered to the patient at least in part based on the CGM reading(s). In various embodiments, doses can be delivered as automated correction boluses and/or automated increases or decreases to a basal rate. Insulin doses can also be administered based on current glucose levels and/or predicted future glucoses levels based on current and past glucose levels.

For example, if the CGM indicates that the user has a high blood glucose level or hyperglycemia, the system can automatically calculate an insulin dose necessary to reduce the user's blood glucose level below a threshold level or to a target level and automatically deliver the dose. Alternatively, the system can automatically suggest a change in therapy upon receiving the CGM data such as an increased insulin basal rate or delivery of a bolus, but can require the user to accept the suggested change prior to delivery rather than automatically delivering the therapy adjustments.

If the CGM data indicates that the user has a low blood glucose level or hypoglycemia, the system can, for example, automatically reduce a basal rate, suggest to the user to reduce a basal rate, automatically deliver or suggest that the user initiate the delivery of an amount of a substance such as, e.g., a hormone (glucagon) to raise the concentration of glucose in the blood, automatically suggest that the user, e.g., ingest carbohydrates and/or take other actions and/or make other suggestions as may be appropriate to address the hypoglycemic condition, singly or in any desired combination or sequence. Such determination can be made by the infusion pump providing therapy or by a separate device that transmits therapy parameters to the infusion pump. In some embodiments, multiple medicaments can be employed in such a system as, for example, a first medicament, e.g., insulin, that lowers blood glucose levels and a second medicament, e.g., glucagon, that raises blood glucose levels.

As with other parameters related to therapy, such thresholds and target values can be stored in memory located in the pump or, if not located in the pump, stored in a separate location and accessible by the pump processor (e.g., "cloud" storage, a smartphone, a CGM, a dedicated controller, a computer, etc., any of which is accessible via a network connection). The pump processor can periodically and/or continually execute instructions for a checking function that accesses these data in memory, compares them with data received from the CGM and acts accordingly to adjust therapy. In further embodiments, rather than the pump determining the therapy parameters, the parameters can be determined by a separate device and transmitted to the pump for execution. In such embodiments, a separate device such as the CGM or a device in communication with the CGM, such as, for example, a smartphone, dedicated controller, electronic tablet, computer, etc. can include a processor programmed to calculate therapy parameters based on the CGM data that then instruct the pump to provide therapy according to the calculated parameters.

Figure 5:
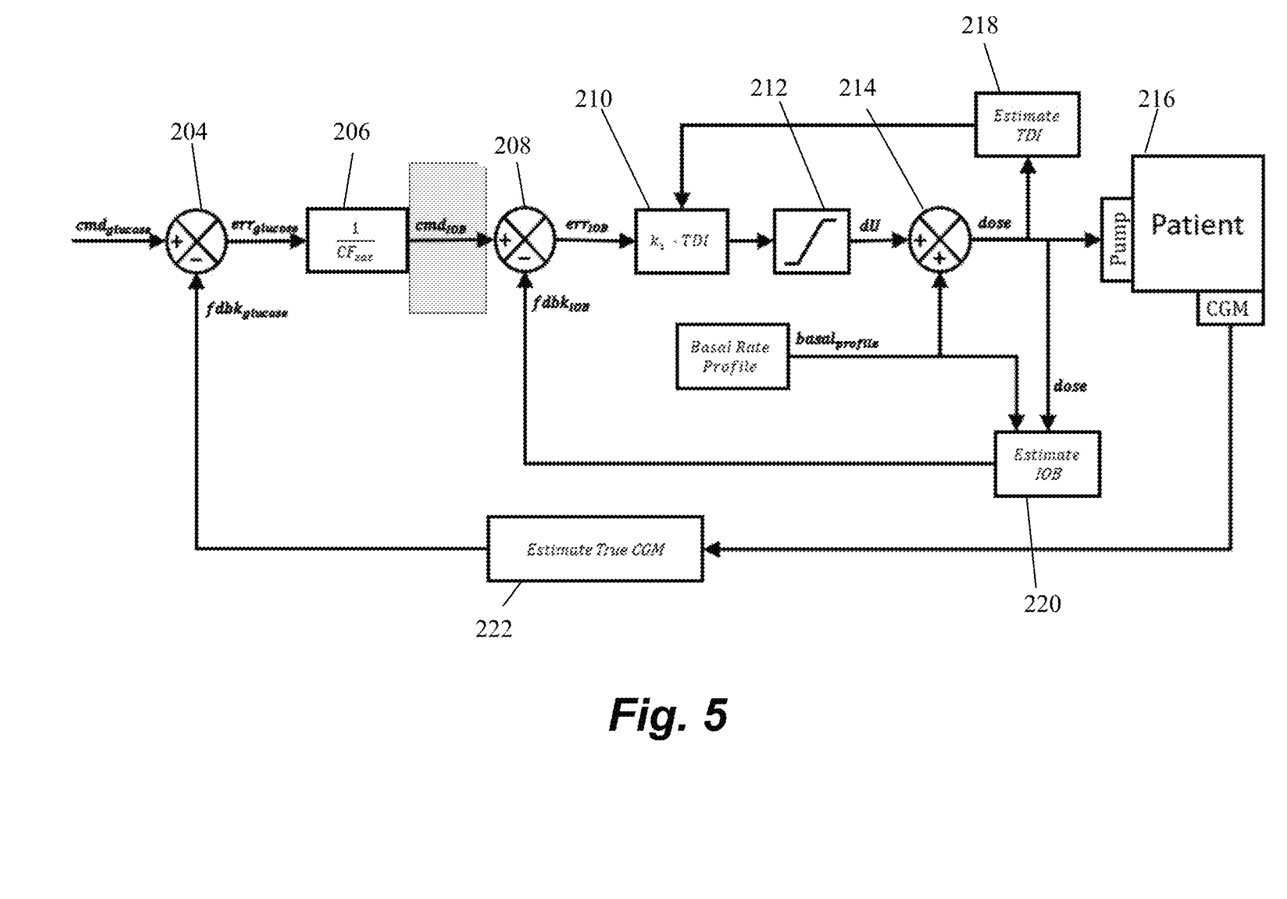
FIG. 5 is a schematic representation of a closed-loop insulin delivery algorithm according to the disclosure.

A schematic representation of a control algorithm for automatically adjusting insulin delivery based on CGM data is depicted in FIG. 5. This figure depicts an algorithm for increasing basal rate that utilizes a cascaded loop. The logic for decreasing basal rate is not depicted. In the depicted embodiment, there is a glucose set-point/command (cmd) that is determined at step 202. The glucose set point is a target value at which the algorithm attempts to maintain a user's blood glucose. This value can vary based on a number of factors, including the user's physiology, whether the user is awake or asleep, how long the user has been awake, etc. The glucose set point is compared to the actual CGM feedback (fdbk) at step 204 to determine a glucose error value (err) that is the difference between the set point and the feedback. The errGLUCOSE value at step 206 is multiplied by a constant (1/CF), in which CF is the user's correction factor, or amount by which one unit of insulin lowers the user's blood glucose. This calculation determines how much insulin is needed to correct the glucose error, which is how much insulin on board (IOB) is needed in the user's body. This IOB value then determines an appropriate estimated insulin on board (IOB) set point for the patient.

The estimated IOB level determined at step 206 is then taken as the command (cmdIOB) for the inner loop and based on a difference of an IOB feedback value (fdbkIOB) and the cmdIOB set point at step 208, an IOB error value (errIOB) is determined. At step 210, the errIOB value is multiplied by a constant k2 (relating to insulin-dependent glucose uptake in the body) and an estimate of the total daily insulin (TDI) of the user. This adjusts the errIOB to be proportional to the constant and the user's total daily intake of insulin. At step 212, a limiter function is applied to the value calculated at step 210. The limiter function prevents the calculated amount from being larger or smaller than preset limits. The result is an insulin amount dU, which is the amount by which the user's stored basal rate should be modified. The insulin delivery rate for the user for the next closed loop interval is therefore calculated by modifying the user's stored basal rate profile by the dU value at step 214.

After the dose is calculated, it can be delivered to the user at step 216 and can also be used to update the estimated TDI for the user at step 218. The dose can also be used to update the estimated IOB level for the user at step 220 by comparing the actual insulin delivered to the programmed basal rate. The updated estimated IOB then becomes the new fdbkIOB for the IOB comparison at step 208. When new CGM values are received from the CGM, an estimated true CGM can be determined based on various factors such as, for example, the calibration status of the CGM sensor, and the estimated true CGM value then becomes the new fdbk-GLUCOSE value for the outer loop comparison with cmd-GLUCOSE at step 204. The algorithm then proceeds through to calculate a new estimated IOB and to the inner IOB loop for calculation of an insulin dose as described above. In one embodiment, a new CGM value is received every 5 minutes and therefore the algorithm executes as set forth above every 5 minutes.

As noted above, some AID systems enable a user to manually enter a "meal announcement" indicating to the system that the user is going to consume a meal. Current systems respond to meal announcements by simply increasing the basal rate dose output by the closed loop algorithm. However, as noted above directly modifying the basal dose from the algorithm can lead to undesirable oscillations in glucose levels. Embodiments of the present disclosure therefore provide an approach to responding to meal announcements in closed loop diabetes therapy that results in more stable glucose levels. Rather than increasing the basal rate open-loop, the IOB set point can be modified within the closed loop algorithm in response to meal announcements. If the user enters a meal announcement, the cmdIOB value used as the set point at comparison step 208 can be increased by a predetermined amount. In one embodiment, the cmdIOB value can be increased by 10%. In embodiments, the predetermined increase could be between, for example, 0% and 500%. For example, if the user's TDI is 100 units/day, the algorithm will attempt to maintain IOB at 6 units (cmdIOB). If the predetermined increase to the IOB set point is 10%, the system would then calculate insulin doses to maintain IOB at 6.6 units. Such an approach essentially increases the IOB tolerance during eating periods and utilizes the stability of the cascaded loop in the closed loop algorithm that relies on CGM values of the user to prevent the oscillations in glucose levels that can occur by simply increasing the basal rate in essentially an open loop manner not incorporating CGM data.

Figure 6:
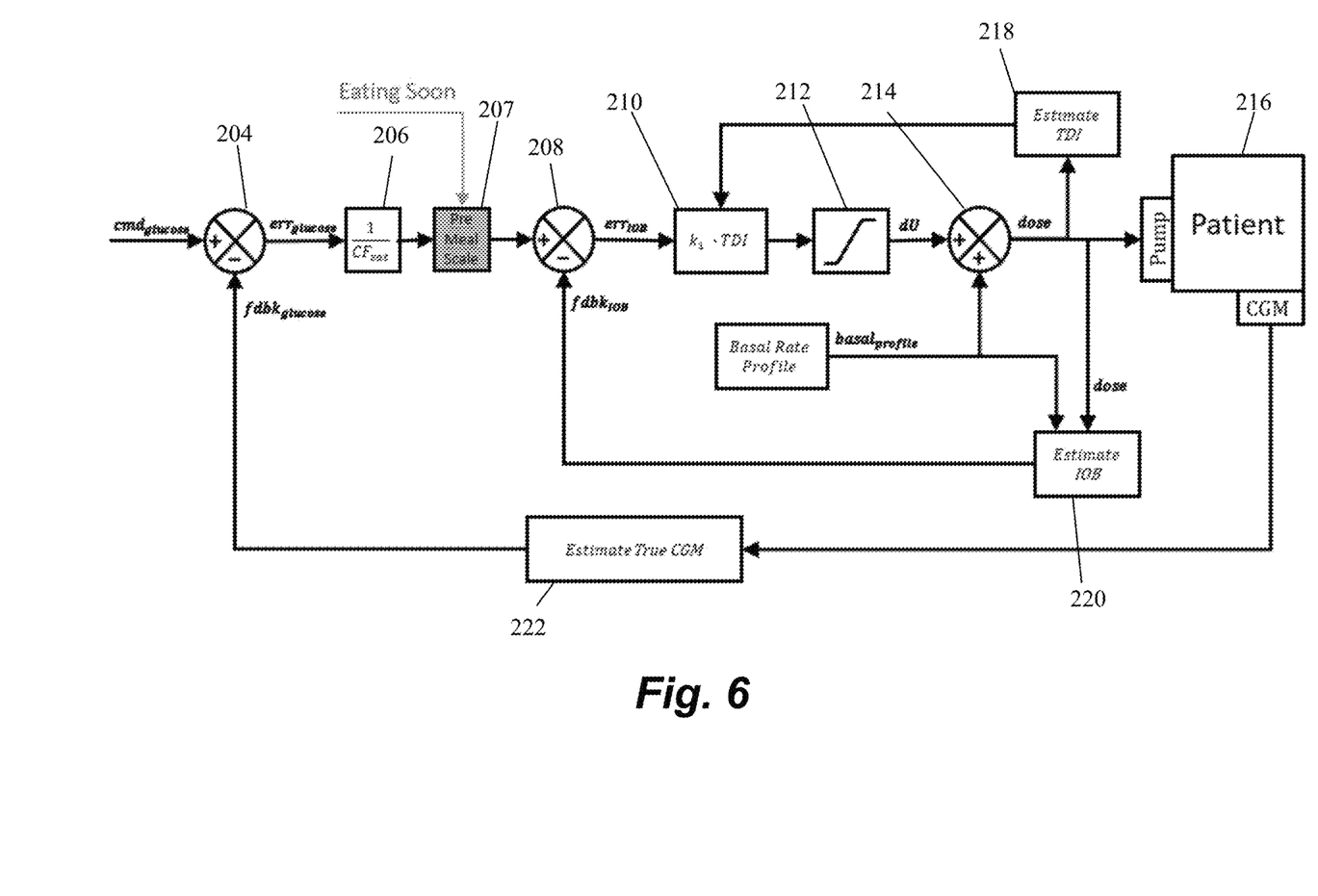
FIG. 6 is a schematic representation of a closed-loop insulin delivery algorithm according to the disclosure.

Referring to FIG. 6, an embodiment of a closed loop algorithm incorporating the IOB set point adjustment for meal announcements is schematically depicted. The algorithm has been modified to include a premeal scale calculation at step 207 that is applied to the cmdIOB value determined in the glucose feedback loop at step 206 and entered into the inner IOB feedback loop at step 208. After determining the initial cmdIOB value as discussed above at step 206, the premeal scale can be applied. The algorithm can determine whether or not a meal announcement was received at step 207. If not, the premeal scale can be set to 1.0 and the cmdIOB value proceeds into the inner loop without being changed. If a meal announcement was made, the premeal scale value can be increased based on the predetermined increase. For example, where the predetermined increase is 10%, the premeal scale is set to 1.1. The algorithm then operates the inner loop with this increased cmdIOB value. The algorithm can continue to execute with the premeal scale activated on each subsequent CGM reading for a predetermined period of time following the meal announcement. In embodiments, the predetermined time over which the premeal scale is activated could be between, for example, 0 to 5 hours. Following the predetermined time after the meal announcement, the algorithm would then return to normal operation with the premeal scale set at 1.0 and not affecting the delivery calculations.

Figure 7:
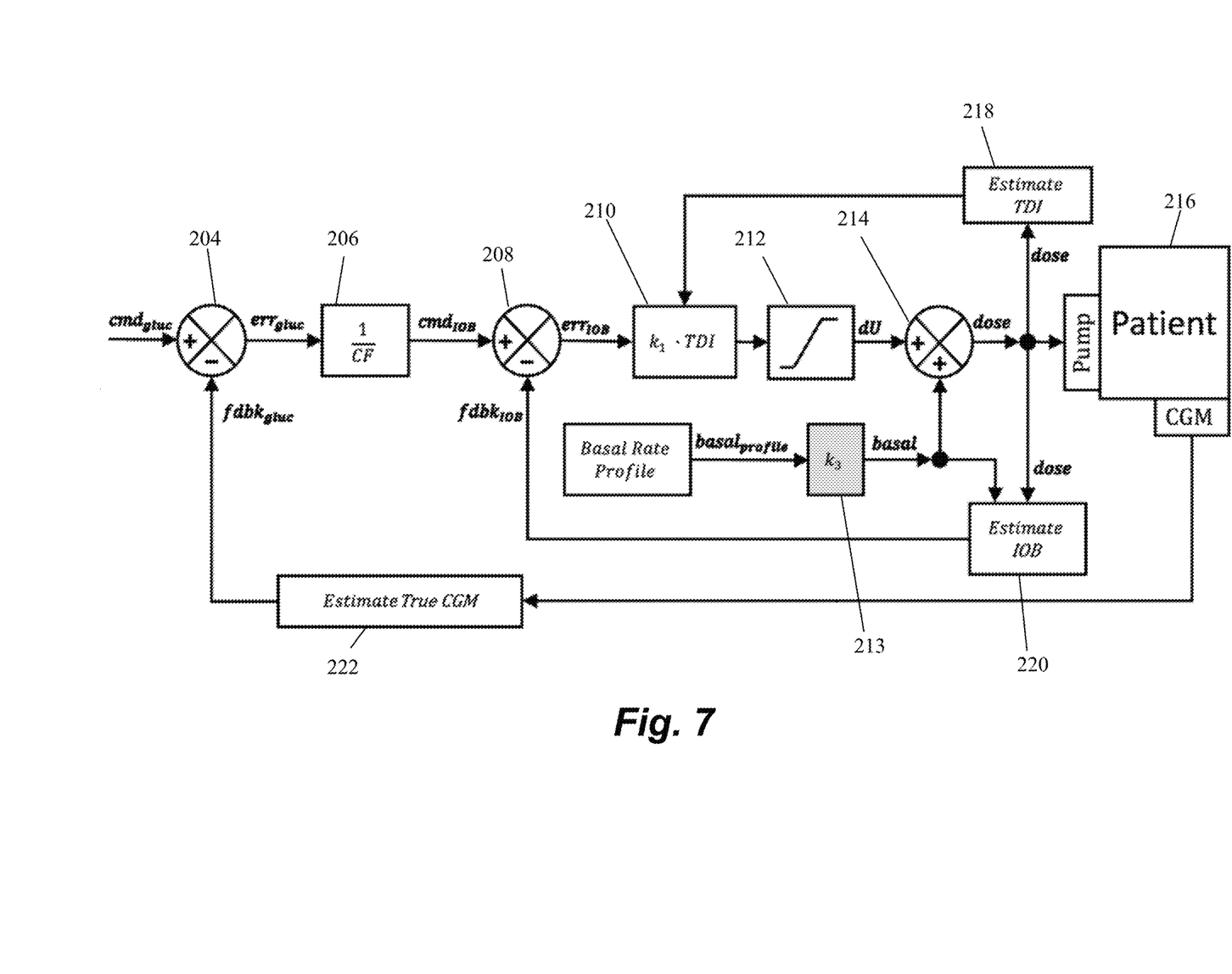
FIG. 7 is a schematic representation of a closed-loop insulin delivery algorithm according to the disclosure.

In another embodiment, the system can alternatively or additionally react to a meal announcement by introducing a temporary basal rate within the inner IOB loop that is used in place of the stored basal profile to calculate the insulin delivery rate at step 214. The temporary rate can be introduced as a constant k3 at step 213 as depicted in FIG. 7 that increases the basal rate used in calculating the delivery rate at step 214 and in estimating IOB at step 220. The IOB estimate is therefore increased in response to the meal announcement because it is estimated based on the increased temporary rate. By inserting the temporary basal rate constant at the depicted location in the algorithm as one part of a broader calculation reacting to glucose measurements, a more stable manner of addressing the meal announcement than simply increasing the calculated dose is provided. As with the premeal scale discussed above, this approach essentially increases the IOB tolerance during eating periods and utilizes the stability of the cascaded loop in the closed loop algorithm to prevent the oscillations in glucose levels that can occur by simply increasing the basal rate open loop. In some embodiments, the k3 constant can be applied to the algorithm in response to a meal announcement in place of the premeal scale described above and in other embodiments the constant can be applied in addition to the premeal scale.

Although embodiments described herein may be discussed in the context of the controlled delivery of insulin, delivery of other medicaments, singly or in combination with one another or with insulin, including, for example, glucagon, pramlintide, etc., as well as other applications are also contemplated. Device and method embodiments discussed herein may be used for pain medication, chemotherapy, iron chelation, immunoglobulin treatment, dextrose or saline IV delivery, treatment of various conditions including, e.g., pulmonary hypertension, or any other suitable indication or application. Non-medical applications are also contemplated.

With regard to the above detailed description, like reference numerals used therein may refer to like elements that may have the same or similar dimensions, materials, and configurations. While particular forms of embodiments have been illustrated and described, it will be apparent that various modifications can be made without departing from the spirit and scope of the embodiments herein. Accordingly, it is not intended that the invention be limited by the forgoing detailed description.

The entirety of each patent, patent application, publication, and document referenced herein is hereby incorporated by reference. Citation of the above patents, patent applications, publications and documents is not an admission that any of the foregoing is pertinent prior art, nor does it constitute any admission as to the contents or date of these documents.

Modifications may be made to the foregoing embodiments without departing from the basic aspects of the technology. Although the technology may have been described in substantial detail with reference to one or more specific embodiments, changes may be made to the embodiments specifically disclosed in this application, yet these modifications and improvements are within the scope and spirit of the technology. The technology illustratively described herein may suitably be practiced in the absence of any element(s) not specifically disclosed herein. The terms and expressions which have been employed are used as terms of description and not of limitation and use of such terms and expressions do not exclude any equivalents of the features shown and described or portions thereof and various modifications are possible within the scope of the technology claimed. Although the present technology has been specifically disclosed by representative embodiments and optional features, modification and variation of the concepts herein disclosed may be made, and such modifications and variations may be considered within the scope of this technology.

The invention claimed is:

1. A system for closed loop diabetes therapy, comprising:
   a pump mechanism configured to facilitate delivery of insulin to a user;
   a communications device adapted to receive glucose levels from a continuous glucose monitor;
   at least one processor functionally linked to the pump mechanism and the communications device, the at least one processor configured to:
   calculate and deliver insulin doses to the user based on a closed loop insulin delivery algorithm, the closed loop insulin delivery algorithm including an outer glucose loop that compares glucose levels from the continuous glucose monitor to a glucose target to determine an insulin on board target for the user and an inner insulin on board loop that compares an estimated insulin on board for the user to the insulin on board target to determine an insulin on board error used to calculate insulin doses configured to maintain the insulin on board of the user at the insulin on board target and the glucose levels of the user at the glucose level target;
   receive an indication that the user will be eating a meal;
   activate a pre-meal scale for the closed loop insulin delivery algorithm in response to the indication that the user will be eating the meal, the pre-meal scale modifying the inner insulin on board loop of the closed loop delivery algorithm that calculates insulin doses to maintain the insulin on board of the user at the insulin on board target; and
   calculate and deliver insulin doses to the user based on glucose levels from the continuous glucose monitor using the pre-meal scale of the closed loop insulin delivery algorithm following the indication that the user will be eating the meal.

2. The system of claim 1, where the pre-meal scale modifies the inner glucose loop of the closed loop delivery algorithm by modifying the insulin on board target of the inner glucose loop.

3. The system of claim 2, wherein the insulin on board target is modified by applying a temporary constant to the insulin on board target to increase the insulin on board target.

4. The system of claim 3, wherein the temporary constant increases the insulin on board target by a predetermined percentage.

5. The system of claim 1, wherein the pre-meal scale is activated for a predetermined period of time following the indication that the user will be eating the meal.

6. The system of claim 1, wherein the indication that the user is eating the meal is received through a user interface communicatively linked with the processor.

7. The system of claim 1, where the pre-meal scale modifies the inner glucose loop of the closed loop delivery algorithm by introducing a temporary basal rate into the inner glucose loop.

8. The system of claim 7, wherein the temporary basal rate is introduced as a constant that increases a stored basal rate used in calculating the estimated insulin on board for the user.

9. The system of claim 1, wherein the pump mechanism and the at least one processor are part of an ambulatory infusion pump.

10. The system of claim 1, wherein the at least one processor is part of a remote control device for remotely controlling an ambulatory infusion pump including the pump mechanism.

11. A method of closed loop diabetes therapy, comprising:
    receiving glucose levels of a user from a continuous glucose monitor;
    calculating insulin doses to the user based on a closed loop insulin delivery algorithm, the closed loop insulin delivery algorithm including an outer glucose loop that compares glucose levels from the continuous glucose monitor to a glucose target to determine an insulin on board target for the user and an inner insulin on board loop that compares an estimated insulin on board for the user to the insulin on board target to determine an insulin on board error used to calculate insulin doses configured to maintain the insulin on board of the user at the insulin on board target and the glucose levels of the user at the glucose level target;
    delivering the calculated insulin doses to the user with a pump mechanism;
    receiving an indication that the user will be eating a meal;
    activating a pre-meal scale for the closed loop insulin delivery algorithm in response to the indication that the user will be eating the meal, the pre-meal scale modifying the inner insulin on board loop of the closed loop delivery algorithm that calculates insulin doses to maintain the insulin on board of the user at the insulin on board target; and calculating and delivering insulin doses to the user based on glucose levels from the continuous glucose monitor using the pre-meal scale of the closed loop insulin delivery algorithm following the indication that the user will be eating the meal.

12. The method of claim 11, where the pre-meal scale modifies the inner glucose loop of the closed loop delivery algorithm by modifying the insulin on board target of the inner glucose loop.

13. The method of claim 12, wherein the insulin on board target is modified by applying a temporary constant to the insulin on board target to increase the insulin on board target.

14. The method of claim 13, wherein the temporary constant increases the insulin on board target by a predetermined percentage.

15. The method of claim 11, wherein the pre-meal scale is activated for a predetermined period of time following the indication that the user will be eating the meal.

16. The method of claim 11, wherein the indication that the user is eating the meal is received through a user interface communicatively linked with the processor.

17. The method of claim 11, where the pre-meal scale modifies the inner glucose loop of the closed loop delivery algorithm by introducing a temporary basal rate into the inner glucose loop.

18. The method of claim 17, wherein the temporary basal rate is introduced as a constant that increases a stored basal rate used in calculating the estimated insulin on board for the user.

19. The method of claim 11, wherein the pump mechanism is part of an ambulatory infusion pump that calculates the insulin doses.

20. The method of claim 11, wherein the insulin doses are calculated by a processor of a remote control device for remotely controlling an ambulatory infusion pump including the pump mechanism.

* * * * *